(12) United States Patent
Casler

(10) Patent No.: US 6,626,800 B1
(45) Date of Patent: Sep. 30, 2003

(54) METHOD OF EXERCISE PRESCRIPTION AND EVALUATION

(76) Inventor: John A. Casler, 1875 S. Beverly Glen., #107, Los Angeles, CA (US) 90025

( * ) Notice: Subject to any disclaimer, the term of this patent is extended or adjusted under 35 U.S.C. 154(b) by 511 days.

(21) Appl. No.: 09/614,962

(22) Filed: Jul. 12, 2000

(51) Int. Cl.[7] .............................................. A63B 21/00
(52) U.S. Cl. ............................................. 482/8; 482/9
(58) Field of Search ..................... 482/1–9, 900–902; 600/300, 520

(56) References Cited

U.S. PATENT DOCUMENTS

| | | | |
|---|---|---|---|
| 5,054,774 A | 10/1991 | Belsito | |
| 5,591,104 A | 1/1997 | Andrus et al. | |
| 5,598,849 A | 2/1997 | Browne | |
| 5,655,997 A | 8/1997 | Greenberg et al. | |
| 5,785,632 A | 7/1998 | Greenberg et al. | |
| 5,810,747 A | 9/1998 | Brudny et al. | |
| 6,450,922 B1 * | 9/2002 | Henderson et al. | 482/8 |
| 6,503,173 B2 * | 1/2003 | Clem | 482/8 |

OTHER PUBLICATIONS

MyFitness.com website samples.
Netpulse website samples.
iFIT.com website samples.
Technogym website samples.
MyFitnessPage.com website samples.

\* cited by examiner

Primary Examiner—Glenn E. Richman

(57) ABSTRACT

An exercise method is disclosed that provides a tailor made exercise protocol that can be modified by a clinician in a supervisory position. A processor with a protocol-generating algorithm is used in communication with an exercise device. Data is input into the processor, such as age, height, weight and sex, and the processor generates an exercise protocol according to a protocol-generating algorithm and the user data. A supervisor is then capable of reviewing and allowing for modification of this exercise protocol. After the exercise protocol is approved it is transferred to the exercise device. A user can then perform an exercise session on the exercise device. Sensors on the device and/or user generate information regarding the exercise session. This information is transferred back to the processor where it is reviewed by the supervisor where the supervisor has the ability to modify the protocol for the next exercise session if they deem it necessary.

20 Claims, 3 Drawing Sheets

METHOD OF EXERCISE PRESCRIPTION AND EVALUATION

BACKGROUND OF THE INVENTION

The invention herein relates to an exercise method and more particularly to a method of presenting an exercise protocol to a user and evaluating the effectiveness of same.

Methods of providing supervisory patient care regarding exercise have only recently been made known. In such systems the supervisor or medical professional is allowed to observe the patient in real time from a remote location. This eliminates down time due to traveling for one or both the supervisor and the user. In some cases physiological data from the user is obtained during the exercise session which can also be evaluated by the supervisor or clinician. Also, some disclosures specify retaining a profile history of the client or user. In any case, though it is theoretically possible for one supervisor to concurrently observe more than one user it is unlikely that one person could adequately observe numerous stations for less obvious discrepancies in performance or exercise form.

The Internet has given birth to a variety of sites that provide a myriad of potentially useful additions to anyone desiring to improve their physical fitness. One such site, iFIT.com, provides for interactive one-on-one personal training. The instructor can walk the user through the training session via a pair of computers, each with video capability.

A site called MyFitness.com gives weather forecasts for your area, for outdoor activity, and provides a training log with links to related web sites. News and other information is also made available through the website. A similar site is MyFitnessPage.com where training stats are made available. In each case this is useful only if someone takes the time to input all the performance data into the computer after or during each training session.

Forms of entertainment have also been used to keep the user from getting bored. Netpulse has made available Internet access to a user while they are undergoing a training session. This is not a training session moderator, simply an aid to keep the user on the cardiovascular training equipment. Since strength-training equipment is used only for a minute or less at a time, this type of assistance is of no value.

Personal on-line training programs or competing in virtual races are aspects of Net Trainer (not yet on the market) by Tecnogym, Inc. The on-line training capacity claims to let you train in your home as you do in a fitness club. This is obviously minus the equipment you would find in the fitness club.

Retrofittable devices are also used to read user data on a weight stack exercise machine. Such a device is intended to read such information as the amount of weight lifted and the distance the weight is moved. This information is transferred to a storage means to be recalled at a later time.

The current state of the art does not anticipate a method of exercise prescription that can generate an exercise protocol, allows a supervisor to view it and if necessary, overwrite or edit the protocol in accordance with the user's requirements. Physiological data such as heart rate, during an exercise session, is often valuable. Performance data is also important to be able to be used to assess the effectiveness of the protocol on the user. This is especially valuable when both physiological and performance data are available to give an assessment.

SUMMARY OF THE INVENTION

Present Invention

In one aspect, the invention features a processor with a protocol generating algorithm and an exercise device in communication with the processor. After inputting user data, such as age, height, weight and sex, into the processor the processor generates an exercise protocol according to the protocol-generating algorithm and the user data. A clinician or supervisor is then capable of reviewing and allowing for modification of this exercise protocol. The approved exercise protocol is transferred to the exercise device. A user then performs an exercise session on the exercise device. Sensors on the device and/or the user generate information regarding the exercise session. This information is transferred to the processor where it is reviewed by the supervisor or clinician.

The system may also include the ability to provide predetermined boundaries to values of the information that is produced during the exercise session. These boundaries allow the execution of an alert when a value of said information is not within these boundaries. Such an alert can be very useful where certain potential medical conditions are associated with this information. An example of this would be if systolic blood pressure went over an amount determined to be safe for a particular individual.

In another aspect, the invention includes a device that provides a processor with a protocol generating algorithm and a display device. An exercise device is used that is in communication with the processor. Upon inputting user data into the processor, an exercise protocol is generated by the protocol-generating algorithm. The protocol is reviewed and allowed to be modified. The protocol is then transferred to the exercise device and an exercise session is performed on said exercise device. One or more sensors on the exercise device provide a generation of information regarding the exercise session. This information is transferred to the processor where can be reviewed.

Definition of Terms

Unless otherwise defined, all technical and scientific terms used herein have the same intended meaning as would be commonly understood by anyone of ordinary skill in the art to which this invention belongs. To eliminate possible ambiguity, specific terms used herein have been defined, as they would be applied to the present invention.

An "Exercise Device" is any device, machine or apparatus that is capable of interacting with a body so as to offer a force in opposition to that of the body. The device may be in the form of a cardiovascular training device that enables prolonged repetitive movements such as an exercise bike or treadmill, a strength training device such as in "weight" training machines or a stretching device that is used to increase the range of motion of one or more joints.

A "Processor" is any computing device that is capable of processing binary data. This includes a personal or desktop computer (PC), a high powered desktop or work station, a laptop computer, palm pilot or any other of a number of computing devices. It is understood that as technology advances in this area the new species of computing devices will generically fall under the scope of this definition.

"Obesity" is a condition characterized by excessive bodily fat.

"Osteoporosis" is a condition that affects especially older woman and is characterized by a decrease in bone mass with decreased density and enlargement of bone spaces producing porosity and fragility.

"Cardio-Pulmonary" conditions include cardiopulmonary diseases relating to the heart and lungs such as lung disease and heart conditions, both preventative and post surgery.

An "Exercise Session" is one complete training session or workout using one or any combination of exercise devices. An exercise session may be comprised of one or more machine sequences.

An "Exercise Protocol" comprises a detailed account of the proposed exercise session. Such detail may include exercise workload, which may include load values of each concentric and eccentric repetition, the anticipated number of repetitions per exercise device, what specific exercise devices will be used in any particular exercise session, and the duration of the use of one or more devices.

A "clinician" is a person skilled in the field of exercise prescription, rehabilitation, medicine, physical therapy, or any other relevant area. A clinician is typically a physician, trainer, physical therapist or physiologist who has a specialty in this area.

DETAILED DESCRIPTION OF THE PREFERRED EMBODIMENT

The object of the disclosed invention is to provide an improved method and device for performing a prescription of exercise that is specific to an individual. This is especially important for those suffering from medical conditions that make certain stresses dangerous to the user. It is also beneficial to the general user in that tailor made training protocols can be used to custom fit a training protocol to a user in order to better fit their individual needs.

Figure 1:
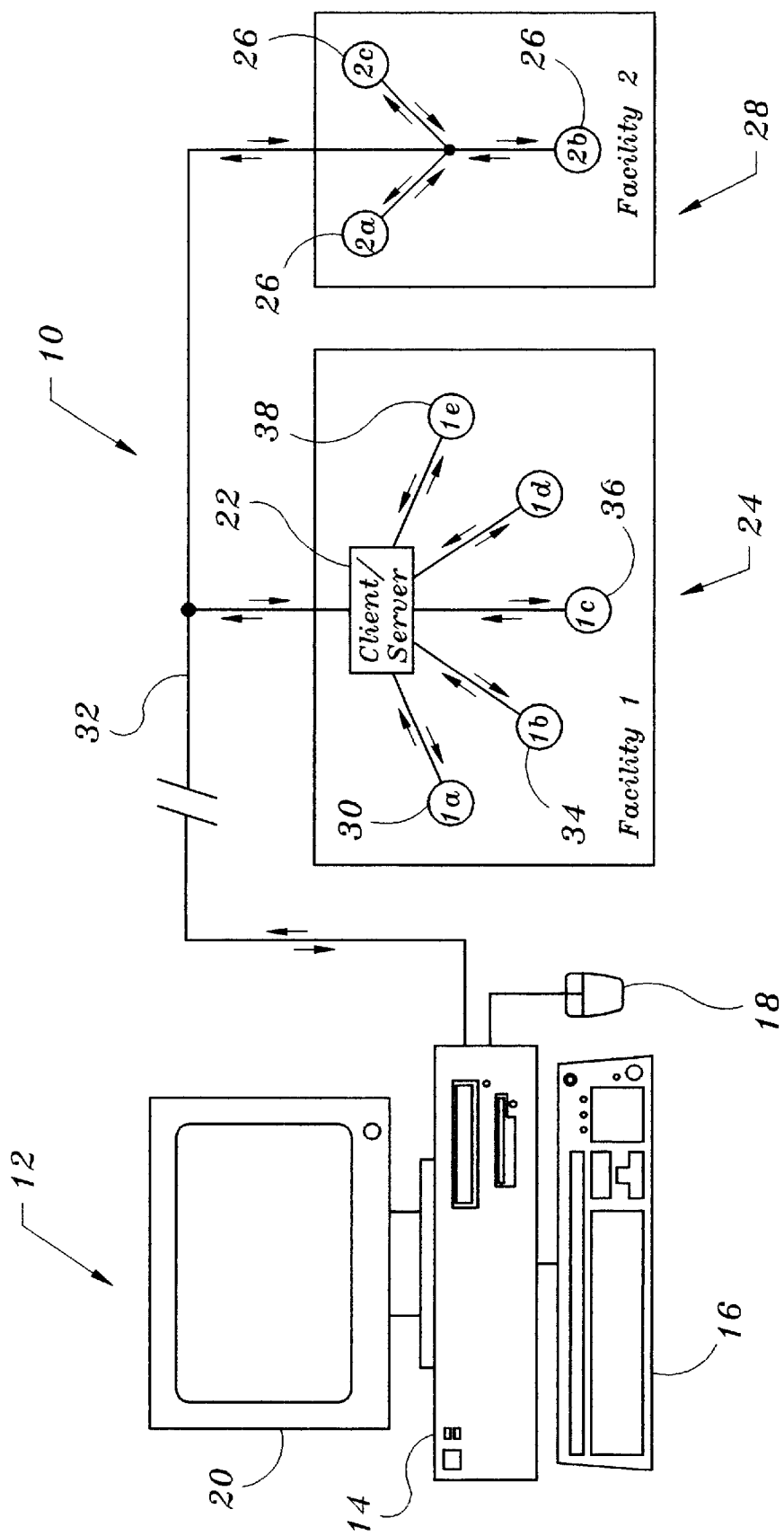
FIG. 1 is a diagram of the equipment used in a typical application of the present invention as produced in accordance with a preferred embodiment.

What is shown in FIG. 1 is a diagram of the equipment 10 as it would typically be used. A computer 12 with a processor 14, and an input device such as a keyboard 16 and mouse 18 are used with a display 20 to enable the supervisor to input data. Though this is shown in the preferred form of a desktop personal computer, this disclosure is not intended to be limited to this form. A laptop computer or even a palm pilot could potentially be used to input and review data.

The computer 12 is shown in communication with a computing device 22 in a first facility 24 and individual devices 26 in a second facility 28. Individual exercise devices 30 are in communication with the computing device 22 at the first facility 24. The functional aspects of the devices 26 at the second facility 28 and the devices 30 at the first facility 24 are identical to the user. Both versions are shown here to illustrate the most obvious variations on the setup of the systems. The computing device 22 at the first facility 24 first acts as a client by receiving information from the computer 12 via the lines 32. These lines could be traditional landlines such as telephone lines (internet or intranet), high-speed digital dedicated lines or a local area network (LAN) line. The airwaves can also function as a "line" through satellite communication.

The information transfer from the computer 12 can take many forms dependent upon the needs at the time. Initial information about the user is processed and reviewed by the supervisor or clinician. An algorithm is used to convert this information into machine codes that initially comprises the information that is transferred from the computer 12 to the computing device 22. This computing device 22 then acts as a server and transfers the pertinent data to each individual device 30. These devices 30 could be versions of the same device, such as more than one identical treadmill, or a series of devices such as a line a strength machines, each unique to work a specific muscle group. For identical devices the machine code could be transferred to each machine awaiting the identification of that particular user. When that particular user identifies himself to a device 30 the specific protocol that was created for that user drives the device 30 to perform the exercise session.

If the devices 30 are comprised of a series of devices that are unique to one another, such as a line of strength equipment, each device would be individually coded to receive only data that is pertinent to that device. For example, if device "1b" 34 is an arm curl machine, and "1c" 36 is a leg press device, the force required to set the arm curl 34 would likely be significantly less than that of the leg press 36. Device "1e" 38 could be an exercise bike and the codes would require a pedal resistance and a duration for the user to perform the exercise session on that device 38. In this arrangement the computing device 22 acts as a server to disseminate the proper information to each device thus enabling proper use of each device for that portion of the exercise session.

The alternative form, as shown in the second facility 28, uses the computer 12 as the server to relay the relevant information regarding each individual device 26. Either form is considered a viable alternative to the other, and either could be deemed preferable in different circumstances. In either case the general function of the elements are similar.

Figure 2A:
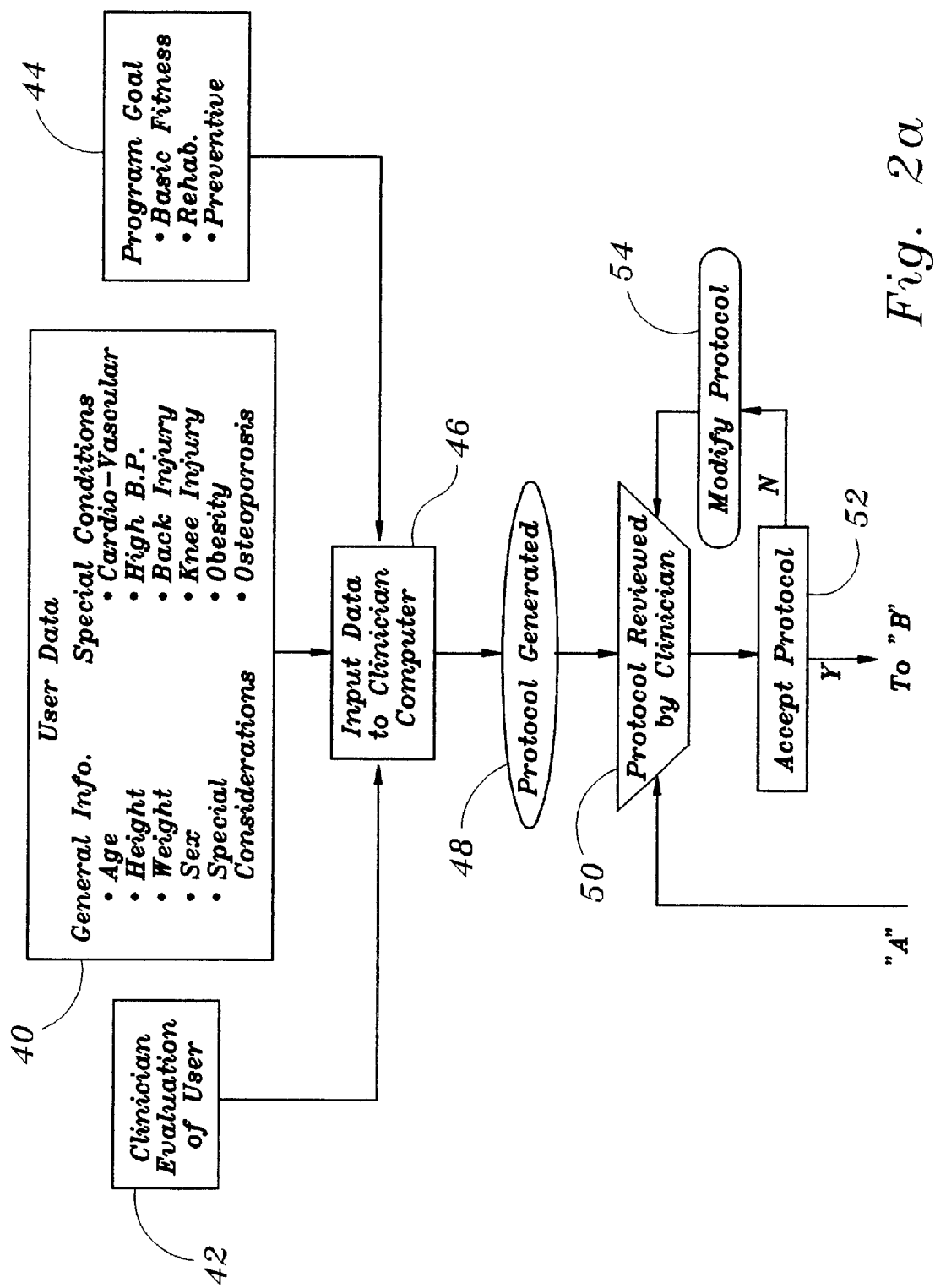
FIG. 2 is a flow chart outlining the steps used in accordance with a preferred embodiment of the present invention.

A flow of information is shown in FIG. 2. The first portion, as shown in FIG. 2a, shows the general information that would be used to determine the user's exercise protocol. Typical "user data" 40 includes the person's age, height, weight, sex and any special considerations such as rehabilitation from injury or cardio-pulmonary disorders, high blood pressure, obesity and osteoporosis, to name a few. A clinician makes an evaluation of the user 42 which can vary from a full physical including a stress test to a brief overview of the user's general physical condition and lifestyle. The goal of the user 44 is also considered in that training to make the Olympic team in weight lifting would be drastically different from someone who is recovering from a heart attack that wants to be able to walk up a flight of stairs.

This information is then put into the clinician computer 46 (computer 12 of FIG. 1) where the afore mentioned information is used in cooperation with one or more algorithms that are specially created to evaluate this information and generate an exercise protocol 48 for that user. This protocol is then displayed to the clinician so that it can be reviewed 50. At this time the clinician can accept the protocol 52 or modify the protocol 54. This process of "tweaking" the protocol is desirable in that though the algorithms are sophisticated, they should not be relied on to replace the clinician, especially in cases where the health of the user is somewhat precarious. Post surgery heart patients would be one of the most obvious to fall within this category. Though the clinician cannot foresee every circumstance, an experienced and well-trained clinician has the ability to see and correct exercise durations or other parameters that would apply only to that user. The generation of the general protocol 48 is highly beneficial in that it saves the clinician a great deal of time.

Figure 2B:
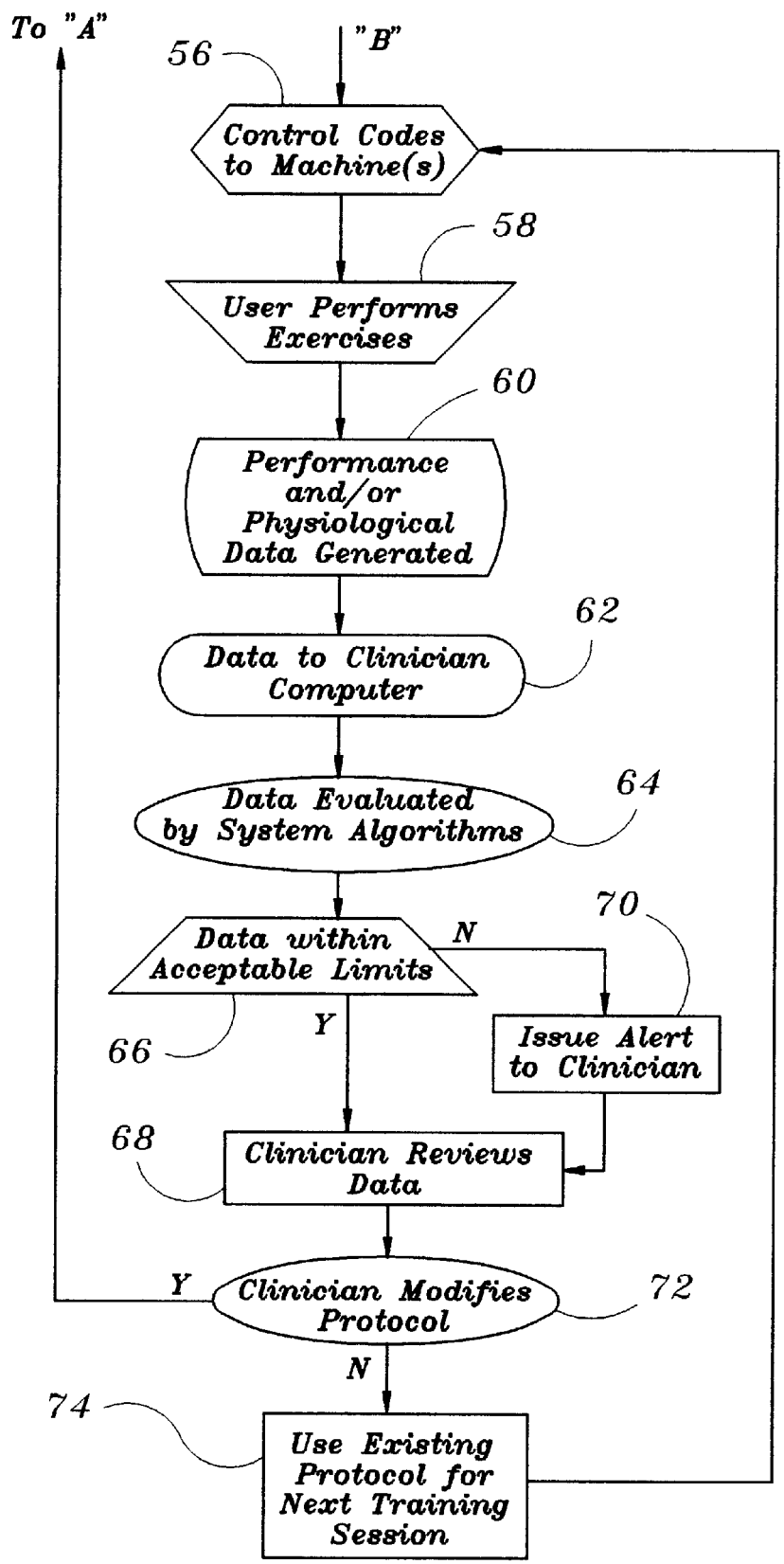

Once the protocol is accepted 52 by the clinician, the clinician computer generates a series of control codes 56 for each relevant machine. This is shown in FIG. 2b. The control codes are transferred to each exercise device that falls within the scope of that protocol. This information is in an electronic form and as such can be easily transferred over long distances or across the room at nearly the speed of light. As such, the user can be in the same building or in another part of the world.

The user simply identifies himself to the exercise device and the relevant protocol is used to control that machine via the control codes. The user then performs the exercise session 58. This can be a single bout or a series of exercise sets, one or more on each of several devices. During the exercise session one or more sensors are used to provide performance and/or physiological data 60 regarding the user's training session. This can be a heart rate monitor, a blood pressure monitor, electrocardiogram (ECG) or any number of sensors placed on the user to give physiological data. In addition, information can be obtained relating to the physical performance during the exercise session. This includes sensors that would likely be mounted on the device itself that would enable feedback as to the physical parameters such as force and distance. This information, with a factor of time, produces power output, work done as well as force and range of motion.

This information is then transferred back to the clinician 62. In this case the exercise device 26 or the computing device 22 acts as the server and the clinician computer 12 is the client (from FIG. 1). System algorithms 64 then analyze this data, preferably within the clinician computer 12. Part of the system algorithms includes boundaries pertinent to specific information. As an example, if the systolic blood pressure of a 60-year-old cardiac rehabilitation patient goes over 200 mm Hg for more then one minute, an alert signal can be sent during the exercise session to the clinician and/or directly to the patient to stop exercising. This could be done via a message line on the display of the device or audibly via speakers directly to the user. This can also apply to general information as well as emergency warnings. For the post training data, these boundaries may be modified to reflect potential warnings or signals as to reduced success or outstanding success in training. If the data is within the acceptable limits 66 the data is sent directly to the clinician to review 68. If any data is not within the preset boundaries, an alert is issued to the clinician to inform them of this occurrence 70, which accompanies the data for the clinician to review 68.

The clinician can review the data and relevant warnings at any time. By a basic analysis of the performance and physiological data, and with the help of the relevant warnings, the clinician can determine if the protocol should be modified for the next training session. If so, the clinician modifies the training protocol 72 and reviews the result 50. This process continues as was previously disclosed herein. If the clinician determines that the existing protocol is sufficient for another training session, it is accepted 74 and the current control codes are prepared to be loaded into the necessary devices in preparation for the next training session.

It is to be understood that all of the enclosed information is presented as the preferred embodiment as seen by the inventor. An infinite number of variations and modifications can be made including the sizing and positioning of the detailed information and forms of graphics used to communicate information to the user.

What is claimed is:
1. An exercise method including the steps of:
 A. providing a processor with a protocol generating algorithm;
 B. providing an exercise device in communication with said processor;
 C. inputting user data into said processor;
 D. generating an exercise protocol according to said protocol generating algorithm and said user data;
 E. reviewing and allowing for modification of said exercise protocol;
 F. transferring said exercise protocol to said exercise device;
 G. performing an exercise session on said exercise device;
 H. generating information regarding said exercise session;
 I. transferring said information to said processor; and
 J. reviewing said information.
2. The method as described in claim 1, further comprising:
 K. modifying said protocol, thus generating a modified protocol;
 L. reviewing said modified protocol; and
 M. transferring said modified protocol to said exercise device.
3. The method as described in claim 2, further comprising:
 N. providing predetermined boundaries to values of said information;
 O. executing an alert when a value of said information is not within said boundaries.
4. The method as described in claim 3, wherein the step of executing an alert is in the form of a message sent to the clinician.
5. The method as described in claim 3, wherein the step of executing an alert is in the form of a message sent to the user.
6. The method as described in claim 5, wherein said message is in the form of a visual message displayed on a message line.
7. The method as described in claim 5, wherein said message is in the form of a audible message.
8. The method as described in claim 1, further comprising:
 K. providing predetermined boundaries to values of said information;
 L. executing an alert when a value of said information is not within said boundaries.
9. The method as described in claim 8, wherein the step of executing an alert is in the form of a message sent to the clinician.
10. The method as described in claim 8, wherein the step of executing an alert is in the form of a message sent to the user.
11. The method as described in claim 10, wherein said message is in the form of a visual message displayed on a message line.
12. The method as described in claim 10, wherein said message is in the form of a audible message.
13. The method as described in claim 1, wherein said data is data selected from the group consisting of age, height, weight, sex and special considerations.
14. The method as described in claim 13, wherein said special considerations are physical conditions.
15. The method as described in claim 14, wherein said physical conditions are conditions selected from the group consisting of low $VO_{2max}$, high blood pressure, obesity, osteoporosis and joint injuries.

16. The method as described in claim 1, wherein step (F) is further comprised of transferring control codes to said exercise device, the control codes enabling a determined performance of said exercise device.

17. The method as described in claim 1, wherein said information is data selected from the group consisting of performance data and physiological data.

18. The method as described in claim 17, wherein said performance data is data selected from the group consisting of machine power output, total work done, speed, force, range of motion and relative perceived exertion.

19. The method as described in claim 17, wherein said physiological data is data selected from the group consisting of blood pressure values and heart rate values.

20. The method as described in claim 1, wherein said communication of step (B) is made by a method of communication selected from the group consisting of a LAN system, and internet system and an intranet system.

* * * * *